United States Patent [19]

Auth et al.

[11] 4,273,127
[45] Jun. 16, 1981

[54] METHOD FOR CUTTING AND COAGULATING TISSUE

[75] Inventors: David C. Auth, Bellevue; Robert F. Rushmer, Seattle, both of Wash.

[73] Assignee: Research Corporation, New York, N.Y.

[21] Appl. No.: 175,322

[22] Filed: Aug. 4, 1980

Related U.S. Application Data

[63] Continuation of Ser. No. 950,694, Oct. 12, 1978, abandoned, which is a continuation-in-part of Ser. No. 656,709, Feb. 9, 1976, Pat. No. 4,126,136.

[51] Int. Cl.³ .............................................. A61B 17/36
[52] U.S. Cl. .............................. 128/303.1; 219/121 L; 331/DIG. 1
[58] Field of Search ................. 128/303.1, 1 R, 395, 128/6, 305, 303.14, 303.17; 219/121 L; 331/DIG. 1

[56] References Cited

U.S. PATENT DOCUMENTS

| 3,865,113 | 2/1975 | Sharon et al. | 128/303.1 |
| 3,982,541 | 9/1976 | L'Esperance | 128/303.1 |

FOREIGN PATENT DOCUMENTS

2646029 4/1978 Fed. Rep. of Germany ........ 128/303.1

*Primary Examiner*—Robert W. Michell
*Assistant Examiner*—Michael H. Thaler

*Attorney, Agent, or Firm*—Seed, Berry, Vernon & Baynham

[57] ABSTRACT

Laser radiation is coupled to an optical instrument having a relatively narrow working edge from which the radiation is emitted in a relatively narrow zone of intense radiation leakage. The working edge is placed in contact with vascularized tissues, and the laser radiation emanating from the working edge in combination with the contact between the working edge and the tissues forms an incision, and the laser radiation photocoagulates tissue adjacent the incision. The contact between the working edge and the tissues accurately positions the laser radiation with respect to the tissue, places pressure on vessels to aid hemostasis, mechanically stresses the incision line and provides the surgeon with tactile feedback. Radiation propagates from a laser to the optical instrument through a low-loss flexible fiber-optic waveguide by means of multimode optical waveguide propagation. As the radiation reaches the working edge of the optical instrument the radiation is emitted from the instrument because the incident angles of individual modes fall below the critical internal reflection angle of the instrument. Radiation leakage is further increased by the presence of blood on the working edge. The frequency of the laser radiation is selected to achieve a desired penetration depth. Deeper penetration may be necessary under some circumstances to produce a clot of sufficient size to allow adequate coagulation. A power control mounted on the handle of the optical instrument or elsewhere allows the surgeon to adjust the intensity of the radiation.

6 Claims, 7 Drawing Figures

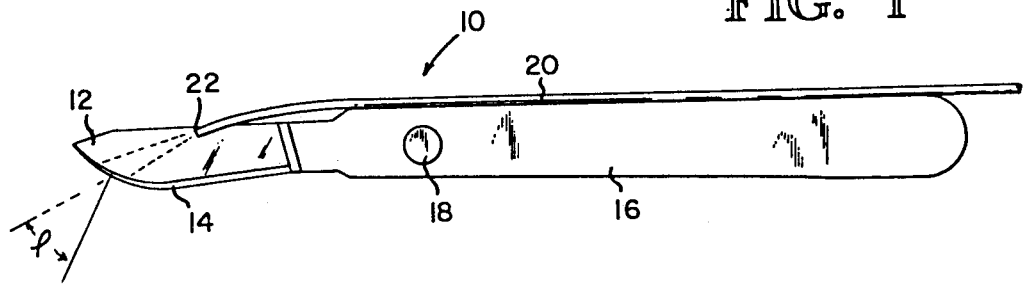
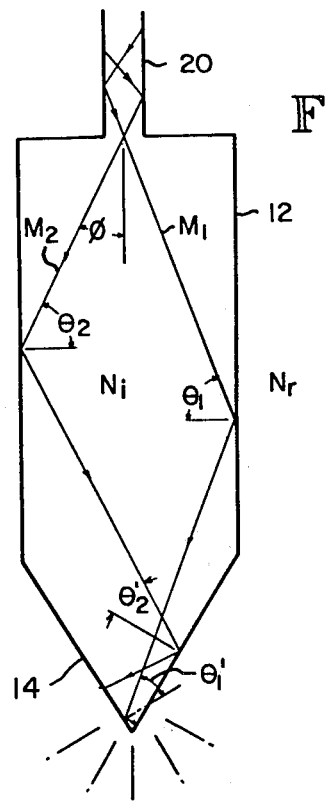
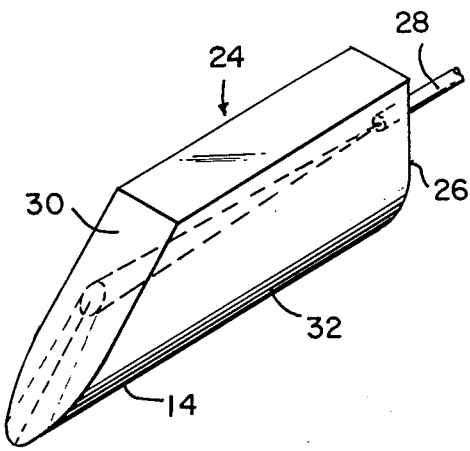
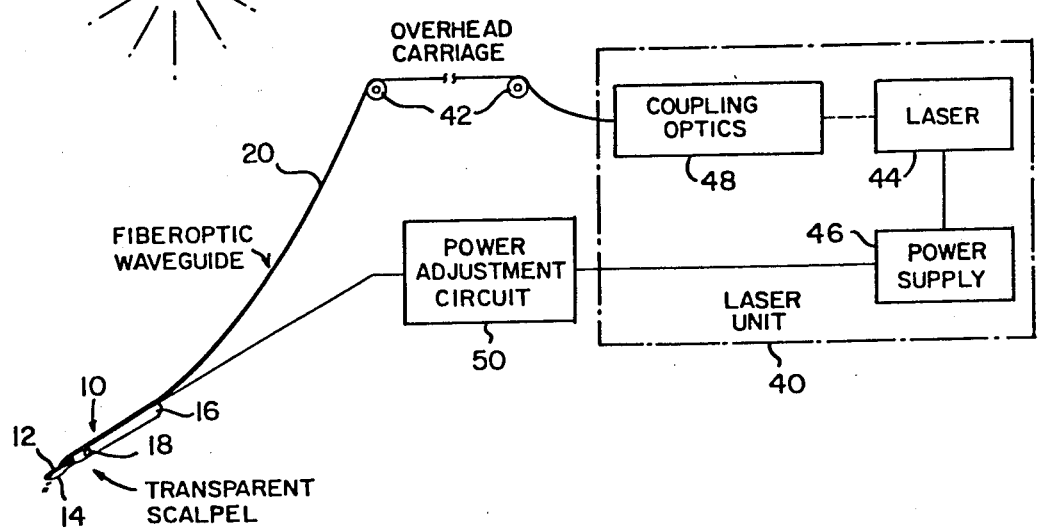

U.S. Patent  Jun. 16, 1981  Sheet 2 of 2  4,273,127
FIG. 5
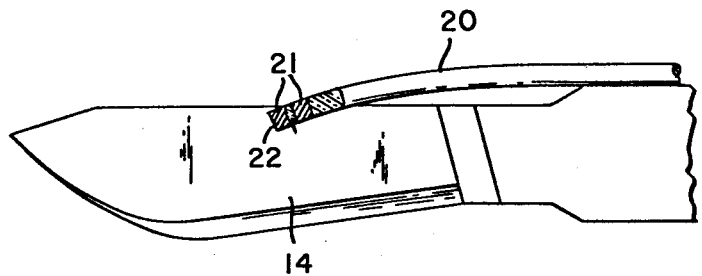
FIG. 6
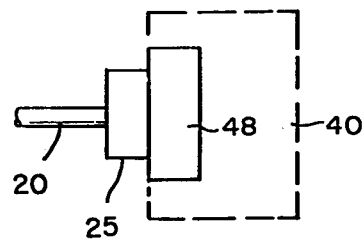
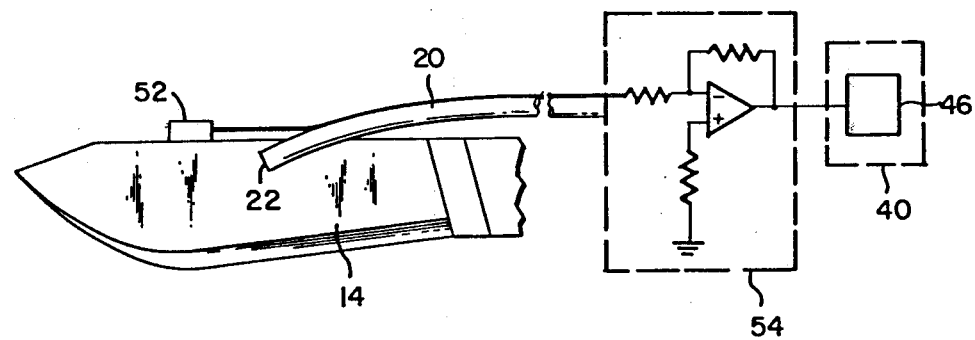
FIG. 7

METHOD FOR CUTTING AND COAGULATING TISSUE

The invention described herein was made in the course of work under a grant or award from the Department of Health, Education and Welfare.

CROSS-REFERENCE TO RELATED APPLICATIONS

This is a continuation of application Ser. No. 950,694 filed Oct. 12, 1978, now abandoned which is a continuation-in-part of application Ser. No. 656,709 filed Feb. 9, 1976, now U.S. Pat. No. 4,126,136.

BACKGROUND OF THE INVENTION

1. Field of the Invention

This invention relates to surgical instruments and, more particularly, to an optical instrument for forming an incision in vascularized tissues and photocoagulating tissue adjacent the incision which has the operating feel similar to a conventional cold scalpel.

2. Description of the Prior Art

A significant problem associated with surgical incisions is the control of bleeding. The problem is particularly acute for surgical removal of burn wound eschar and in surgery of highly vascularized organs such as the liver.

An important factor in the development of burn wound sepsis is the dead tissue of deeply burned areas which completely lose their resistance to invading bacteria. It has long been recognized that prompt, safe removal of the dead tissue is desirable not only to prevent infection but also to promote more rapid wound cover with autograft or homograft. Attempts to remove dead tissue by chemical and surgical means have been made. Surgical removal has been carried out effectively, but with the attendant drawback of large blood losses necessitating extensive transfusions. Therefore, the immediate and complete surgical excision of deep burns is generally limited to patients with moderate sized burns. In summary, earlier grafting is capable of markedly decreasing the incidence of bacterial wound sepsis, diminishing the hypermetabolic response of the severely-burned patient thereby resulting in a shortened hospital admission and allowing improved functional and cosmetic results.

Similar problems are associated with surgery on highly vascularized organs. Massive hemorrhage is sometimes a complication from small resections or even biopsies of the liver.

The use of focused laser radiation to incise and coagulate tissue has been widely considered, although such techniques have not been altogether satisfactory. Surgeons are generally accustomed to the tactile feedback that conventional tissue contacting scalpels provide, and they are reluctant to utilize an operating technique in which the surgical instrument is held above and apart from the tissue to be cut. Additionally, it is often difficult to accurately position the laser radiation. Inadvertent deposition of laser radiation away from the incision line may thus cause thermal necrosis to viable cells.

Another surgical device which attempts to simultaneously incise and coagulate tissue is the diathermy scalpel which utilizes high-frequency electrical current for hemostatic incisions. The principal disadvantage of this device is its inadequate hemostasis in several types of surgery. Other disadvantages include unwanted thermal necrosis and hazards associated with electrical shocks. Furthermore, there may be some tendency for the diathermy electrode to adhere to highly-vascularized organs since removal of an electrocoagulating electrode from the cut surface of a liver has, in some cases, reactivated bleeding.

Hemostatic incisions have also been attempted using a plasma scalpel in which a stream of high-temperature gases are directed at the tissue surface in order to form the incision and coagulate tissue adjacent the incision. It has been suggested that plasma scalpels also exhibit slow excision rates and thermal necrosis. Furthermore, plasma gas embolization has been reported following surgery with the plasma scalpel.

SUMMARY OF THE INVENTION

The primary object of this invention is to prevent blood loss during surgery, particularly losses resulting from excision of burn wounds or surgery on highly-vascularized organs.

It is another object of this invention to provide an optical surgery technique which causes rapid hemostasis while limiting necrosis of incised tissue.

It is another object of the invention to provide an optical surgery device and method which provides the surgeon with tactile feedback thereby producing a familiar operating feel.

It is still another object of the invention to provide an optical surgery technique system which cuts tissue with a speed comparable to conventional, non-coagulating scalpels.

It is a further object of the invention to provide an optical surgery technique which facilitates rapid healing of the incision and which has no adverse biological affects such as a tendency to cause embolization.

These and other objects of the invention are provided by coupling laser radiation to a light guide having a relatively narrow working surface from which the radiation is emitted with a fairly high divergence angle in a relatively narrow zone of intense radiation leakage. The working surface is placed in contact with tissue and the laser radiation in combination with the contact between the working surface and the tissue forms an incision, and the laser radiation coagulates tissue adjacent the incision. The contact between the working surface and tissue is preferably sufficient to mechanically stress the tissue so that the incision is formed along the stress zone and to apply pressure to vessels to facilitate coagulation. The frequency of the laser radiation is selected to achieve a desired depth of penetration of the laser radiation into the tissue.

BRIEF DESCRIPTION OF THE DRAWINGS

FIG. 1 is a side elevational view of the cutting and coagulating device including an optical instrument having a light-emitting working edge receiving laser radiation through a fiberoptic waveguide.

FIG. 2 is a schematic illustrating the propagation path of two modes of laser radiation through the section 2—2 of the instrument of FIG. 1.

FIG. 3 is a schematic for the cutting and coagulating device.

FIG. 4 is an isometric view of an alternative embodidment of the optical instrument.

FIG. 5 is a schematic of the cutting and coagulating device including a low-loss index matching medium and an optical element positioned between the light guide and waveguide.

FIG. 6 is a schematic illustrating the use of an optical element positioned between the laser unit and waveguide.

FIG. 7 is a schematic illustrating an alternative embodiment of a power control system for the laser unit.

DETAILED DESCRIPTION OF THE INVENTION

The optical instrument 10, forming part of the cutting and coagulating device is illustrated in FIG. 1. The instrument includes a transparent light guide 12 having a relatively narrow working surface or edge 14. The light guide 12 is mounted at the end of a conventionally-shaped scalpel handle 16. Although the power delivered by the laser may be constant, it may be desirable to control the power through a pressure-sensitive control 18 or similar device for adjusting the intensity of the laser radiation delivered to the guide 12. A fiberoptic waveguide 20 is optically coupled at one end to the guide 12 so that laser radiation is injected into the transparent guide 12 and then propagates to the working edge 14 where it is emitted from the light guide 12. The light guide 12 may be formed by a variety of non-hygroscopic, transparent materials having high resistance to thermal shock and a low optical absorption coefficient. In one operational embodiment fused quartz having a melting point of about 1610° C., a coefficient of thermal expansion of about $0.56 \times 10^{-6}/°C.$ and working surface having a width of about 1.3 mm. was advantageously used.

The fiberoptic waveguide 20 which transports laser radiation to the lightguide 12, is flexible, light in weight and relatively rugged, particularly when encased in polyethelene tubing. Because of the high power density of the laser radiation, the waveguide 20 must have low-loss characteristics in order to avoid destruction of the fiber. One type of optical waveguide which may be advantageously used is a step index, cylindrical quartz-glass fiber which is available from the Corning Glass Company. The quartz fiber is encapsulated in a laminated sheath of non-toxic polyethelene which may also contain leads (not shown) connected to the power control 18. The coupling of the waveguide 20 to the light guide 12 requires a low-loss medium capable of withstanding the very high power densities at the exit point of the waveguide 20. A variety of coupling schemes are possible. A butt joint using epoxy, cyanoacrylate or resin cement as a low-loss bonding agent 21 as illustrated in FIG. 5 provides mechanical strength as well as optical transparency. The bonding agent 21 preferably has an index of refraction intermediate the indexes of refraction of the light guide 12 and waveguide 20 in order to minimize reflection of the incident radiation from the light guide 12. Alternatively, an index matching fluid or air coupling may be utilized with a mechanical supporting member. In general, the waveguide 20 should meet the light guide 12 perpendicularly in order to provide optimum coupling. Various techniques for inclining the fiber waveguide to the blade axis can be employed. For example, as illustrated in FIG. 1, a V-shaped notch 22 can be formed at the top of the light guide 12 for receiving the end of the waveguide 20. The injection angle, $\phi$, i.e. the angle between the illuminating cone axis and the plane perpendicular to the working edge may be varied to provide optimum results as explained hereinafter.

The handle 16, to which the light guide 12 is secured, is of conventional shape and materials. The forward portion of the handle 16 may include a pressure-sensitive power control 18 which may be a variable resistor or variable capacitor. Leads (not shown) are connected to the control 18 and are preferably routed through a jacket enclosing the waveguide 20.

A schematic illustrating the manner in which the laser radiation propagates to the working edge 14 is shown in FIG. 2. When a ray of light strikes an interface between substances having different indexes of refraction, the ray is refracted or bent. The angle of refraction $\theta_r$ is defined by Snell's law as being arcsin $N_i/N_r$ Sin $\theta_i$ where $\theta_i$ is the angle of incidence, and $N_i$ and $N_r$ (FIG. 2) are the indices of refraction in the first and second mediums, respectively. When the angle of refraction ($\theta_r$) reaches 90° the angle of incidence ($\theta_i$) is equal to the "critical angle". For angles of incidence in excess of the critical angle, essentially all of the light is internally reflected. The critical angle $\theta_c$ is equal to arcsin $N_r/N_i$. As illustrated in FIG. 2, a ray of light $M_1$ injected into the light guide 12 strikes the guide surface at an angle $\theta_1$ which is greater than the critical angle $\theta_c$. Consequently, all of the incident radiation is internally reflected. As the ray $M_1$ propagates toward the tapered working edge 14 it continues to be internally reflected from the parallel surfaces of the light guide 12. At the working edge 14, however, the angle of incidence $\theta_1'$ is less than the critical angle $\theta_c$ and part of the incident radiation is emitted from the light guide 12 in a relatively narrow zone of intense radiation. Although the working edge from which the light is emitted is relatively narrow, the divergence angle of the radiation is preferably relatively large, i.e. the radiation diverges from the narrow working edge in diverse directions. This feature allows the incision to be relatively narrow yet spreads the coagulating radiation over a wide angle. Similarly, the ray of light $M_2$ has an angle of incidence $\theta_2$ at the upper portion of the light guide 12 which is greater than the critical angle $\theta_c$ so that all of the incident radiation is internally reflected. When the ray strikes the surface of the beveled working edge 14, its angle of incidence $\theta_2$ is less than the critical angle and some of the incident radiation is emitted from the light guide 12. Although the light guide 12 is illustrated as having a fairly sharp working edge 14, it is important to note that substantially blunter edges may also be employed since it is the laser radiation in combination with the mechanical stress provided by the edge which forms the incision. The major significance of the contact between the working edged 14 and tissue is to accurately position the laser radiation where the incision is desired unlike conventional laser scalpels in which the radiation is focused onto tissue from a distance above the tissue. Also, the contact between the light guide 12 and tissue allows blood to contact the working edge 14 thereby improving the coupling of the laser radiation to vascularized tissue since the blood reduces the critical angle in the light guide 12 and increases local absorption. Finally, the contact between the light guide 12 and tissue provides the surgeon with tactile feedback which realistically simulates the tactile feedback of a conventional cold, sharp-edged scalpel. Thus, use of the light guide 12 provides a familiar operating feel. The light guide 12 is preferably used in a manner so that the contact between the working edge 14 and tissue is sufficient to mechanically stress the tissue. When laser radiation is then emitted from the edge in a relatively narrow zone of intense radiation the radiation applied to the stress zone causes the tissue to fall away or part to form an incision. Also the working edge 14 applies pressure to vessels which stagnates blood flow thereby improving clot formation. Without this pressure, heat may be carried away by blood flow at an excessive rate thereby preventing a clot from forming unless excessive, and potentially damaging, radiation intensities are used. The width of zone of intense radiation leakage from the working edge 14 is preferably less than 5 mm since wider radiation patterns are inefficient and may produce excessive necrosis.

In practice, the laser radiation injected into the light guide 12 from the fiberoptic waveguide 20 has a relatively narrow illumination cone. The cone is defined as having a numerical aperture equal to $\eta \sin \phi$ where $\phi$ is the half angle of the angle of the cone of convergence and $\eta$ is the index of refraction of the medium in which the cone is measured. The numerical aperture of the illuminating cone is restricted so that the minimum angle of incidence of the light rays is set above the critical internal reflection angle so that all of the radiation is internally reflected in the parallel sided portion of the light guide 12.

For clarity of illustration, only two rays $M_1$, $M_2$ are illustrated in FIG. 2. In actuality, a continuum of such rays can exist, each having a particular propagation angle or angle of incidence to the blade surface. The selection of angles excited in the light guide is determined by the angular spectrum of rays in the waveguide. In order to prevent premature radiation leakage, propagating rays having an angle of incidence less than the critical angle are restricted by restricting the numerical aperture at which the radiation is injected into the light guide 12. This numerical aperture restriction can be accomplished by placing an optical element 23 between the fiberoptic waveguide 20 and light guide 12 as illustrated in FIG. 5 to redistribute the intensity profile of excited rays in order to achieve a particular rate and distribution of leakage at the working edge 14. These optical elements 23 may include such devices as lenses, prisms, gratings, polarizers, etc., which manipulate the relative angular spectral weighting of the injected radiation. Alternatively, the numerical aperture at which the laser radiation is injected into the waveguide may be restricted since restricting the angular spectrum of rays which are excited in the waveguide 20 restricts the angular spectrum of rays which can be excited in the light guide 12. One example of this alternative embodiment is illustrated in FIG. 6. A conventional optical element 25 such as a lens, prism, grating, etc. is placed between the coupling optics 48 waveguide 20. As the laser radiation propagates in the tapered zone near the working edge 14, it partially leaks out of the light guide 12 as ray angle conversion occurs and individual ray vectors fall below the critical internal reflection angle. The leakage will be enhanced by the presence of blood on the blade surface since the optical index of refraction of blood is substantially higher than air and, hence, increases the magnitude of the critical angle.

The rate and position of the radiation leakage can also be modified by adjusting the shape of the working edge 14 such as its taper angle and profile, as well as the index of refraction of the light guide. For example, a material may have a critical angle for total internal reflection with air as the external medium of about 35°. When a light guide fabricated of such material is immersed in water, the critical angle may increase to about 49°. Intermediate angle rays excited in the light guide 12 having angles of incidence between 35° and 49° would be partially emitted from the light guide if the guide 12 were immersed in water or blood, but would propagate without significant loss if the light guide 12 were surrounded by air. Rays having angles of incidence greater than 49° would be totally internally reflected even if the light guide 12 was immersed in water. However, as the rays propagate and sustain multiple reflections in the tapered zone of the working edge 14, ray angle conversion occurs and the angle of incidence of the rays with the surface of the light guide varies. Thus, those rays having angles of incidence greater than 49° in the portion of the light guide 12 having parallel sides would experience angular shifts in the tapered zone of the working edge 14 and begin to experience partial leakage from light guide 12 as their incident angles drop below the critical angle for the particular external medium. It is apparent that a particular leakage profile can be obtained by proper arrangement of the rays which are excited at the point of injection. The injection angle $\phi$ (FIG. 1) may also be adjusted to vary the characteristics of the laser radiation emitted from the light guide. However, if the injection angle $\phi$ is too large the injected radiation is reflected from the working edge 14 since its angle of incidence may become greater than the critical internal reflection angle at the working edge 14 of the light guide 12.

The light guide may assume configurations other than that illustrated in FIGS. 1 and 2. For example the light guide may be cylindrical with radiation being emitted from its end which may be pointed. One alternative embodiment of a light guide is illustrated in FIG. 4. Laser radiation is injected into the light guide 24 at an end face 26 through a fiberoptic waveguide 28. The radiation propagates by means of multimode waveguide propagation along the longitudinal axis of the light guide 24 and is reflected from an angled end wall 30 toward the working edge 32 of the light guide 24. If desired, the end wall may be curved to provide a predetermined reflection pattern such as a relatively wide dispersion of the radiation. Note that the working edge 32 is rounded and thus substantially blunter than the working edge 14 of the light guide 12 illustrated in FIG. 1.

A schematic of the overall cutting and coagulating device is illustrated in FIG. 3. The transparent light guide 12 of the optical instrument 10 is optically coupled to the fiberoptic waveguide 20 which extends to a laser unit 40. The waveguide 20 may be supported between the optical instrument 10 and laser unit 40 by an overhead carriage 42 or support arm. The laser unit 40 includes a laser 44 connected to an adjustable power supply 46. Since the laser beam is generally substantially wider than the waveguide 20, coupling optics 48 are placed between the laser 44 and waveguide 20 to reduce the width of the laser beam to fit within the width of the waveguide 20. The coupling optics 48 may also be used to adjust the characteristics of the laser radiation entering the waveguide 20 such as, for example, to restrict the numerical aperture of the radiation as previously explained.

The power supplied to the laser 44 by the power supply 46 may be controlled to adjust the intensity of the laser radiation from the laser 44 in order to ensure rapid cutting and coagulation without causing undue necrosis. For this purpose, a power adjustment system includes a pressure-sensitive power control 18 on the handle 16 which may be a commercially available pressure-sensitive resistor or capacitor. The power control 18 is connected by leads (not shown) to a power adjustment circuit 50 which converts the output of the control 18 to a voltage for modulating the conventional power modulation input of the laser power supply 46. For example, the power adjustment circuit 50 may be a DC voltage source connected to the ends of a variable resistor with the resistor center tap connected to the power supply 46. Alternative power control systems may also be devised which automatically set the intensity of the laser radiation to an optimum value. One such system as illustrated in FIG. 7 includes a sensor 52 for measuring the laser radiation internally reflected from the working edge 14 toward the waveguide 20. The optical sensor is preferably placed at the top portion of the light guide 12. An excessive amount of internally reflected light indicates that laser radiation is of an intensity greater than can be absorbed by blood emanating from the incised tissues. The power control system provides voltage to the power modulation input of the laser power supply which maintains the intensity of the internally reflected light relatively constant. This may be accomplished simply by connecting the output of the optical sensor to an inverting amplifier 54 which produces a voltage inversely proportional to the voltage at the output of the sensor 52. The output of the amplifier is connected to the power supply 46 of the laser unit 40 in the same manner as the power adjustment circuit 50 of FIG. 3.

In operation, laser radiation is delivered to the light guide 12 of the optical instrument 10 through the fiber-optic waveguide 20. The working edge 14 of the optical instrument is placed in contact with the tissue in which the incision is to be formed thereby mechanically stressing the incision line and providing the surgeon with tactile feedback. It is important to note, however, that it is not necessary to mechanically stress the incision line since incisions can be formed with only light pressure of the light guide 12 against the tissue. The laser radiation emitted from the light guide 12 adjacent the working edge 14 then forms an incision in the mechanically stressed tissue and coagulates blood emanating from the incised tissues. At the same time the light guide 12 contacting the tissue applies pressure to vessels thereby aiding hemostasis and blood on the surface of the working edge 14 facilitates coupling of laser radiation from the light guide 12 to the tissues. By adjusting the pressure on the control element 18, the surgeon may control the amount of laser radiation delivered to the light guide 12 depending upon the quantity of blood present which must be coagulated.

The laser unit 40 must be capable of producing laser radiation having an intensity sufficient to rapidly form an incision and coagulate blood. A 50 watt continuous wave Nd:YAG laser has been adequate for this purpose. Although the invention should not be considered as being limited to any particular type of laser, a conventional Nd:YAG laser appears most desirable for deep penetration since it emits radiation having a wavelength which penetrates a moderate distance into the incised tissue, can be transmitted through a flexible quartz waveguide with relatively low loss, and is available in sufficiently high continuous powers to enable rapid coagulation. Where relatively slight penetration is desired an argon laser may be employed. The radiation from an argon laser is more readily absorbed by vascularized tissue than Nd:YAG laser radiation and thus penetrates to a shallower depth. While either the Nd:YAG or argon laser radiation is absorbed by red hemoglobin, it is only mildly absorbed by white tissue thereby reducing the amount of necrosis in the tissue surrounding the incision while providing adequate energy to the red hemoglobin to arrest bleeding.

The frequency of the radiation injected into the waveguide 20 may be outside the visible spectrum including infra-red and ultraviolet radiation. Although the use of a transparent light guide optically coupled to a laser is the preferred embodiment, other systems for emitting laser radiation in a relatively narrow zone while mechanically stressing the tissue to be incised may also be employed. For example, a plurality of spaced apart optical waveguides coupled to a laser may be embedded in an opaque or transparent stressing element with the waveguides terminating at or near a working edge formed in the stressing element.

The cutting and coagulating device may also be used solely for coagulation. In this technique the light guide 12 is inclined at an angle to the tissue to be coagulated and a lateral portion of the working surface is placed in contact with the tissue. The laser radiation is thus directed to the tissue contacting the light guide and the pressure of the light guide against the tissue pinches blood vessels to facilitate coagulation.

The cutting and coagulating device of the present invention can advantageously be used for relatively bloodless surgery without such disadvantages as tissue necrosis and slow operation associated with prior art devices, even for such problem surgery as burn wound removal and surgery on highly-vascularized organs such as the liver.

We claim:

1. A method of creating an incision in vascularized tissue and coagulating tissue adjacent the incision comprising coupling laser radiation to a light guide having a relatively narrow working surface which is elongated in the direction of the incision from which said radiation is emitted in a beam and which has a relatively large angle of divergence in a plane perpendicular to said incision, and guiding said working surface along and in contact with said tissue, said laser radiation being of sufficient intensity to form said incision so that said laser radiation forms said incision at the point of contact between said working surface and tissue and coagulates blood adjacent said incision while the contact between said working surface and tissue provides tactile feedback and facilitates coupling of laser radiation from said light guide to said tissue.

2. The method of claim 1 wherein said working surface is less than 5 mm. in width in order to minimize necrosis of said tissue and provide rapid tissue separation.

3. The method of claim 1 wherein the force applied to said light guide toward said tissue is sufficient to mechanically stress said tissue thereby forming said incision along said stress zone and to apply pressure to vessels in said tissue to facilitate coagulation.

4. The method of claim 1 wherein the frequency of said laser radiation is selected to achieve a predetermined depth of penetration in said tissue.

5. The method of claim 4 wherein said radiation is generated by a Nd:YAG laser thereby achieving a relatively large depth of penetration of said radiation in said tissue.

6. The method of claim 4 wherein said radiation is generated by an argon laser thereby achieving a relatively slight depth of penetration of said radiation in said tissue.

* * * * *